Figure 2:
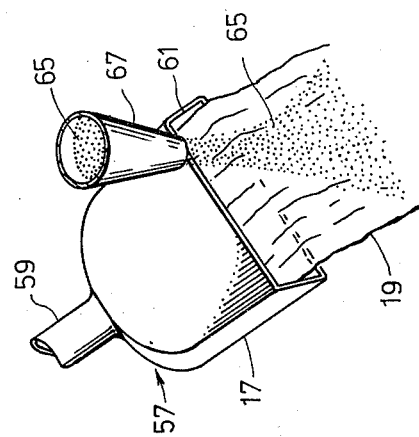

United States Patent [19]

Gibbons

[11] 4,405,399
[45] Sep. 20, 1983

[54] METHOD AND APPARATUS FOR MANUFACTURING DENTIFRICE CONTAINING DISPERSED SPECKLES

[75] Inventor: Edward J. Gibbons, Scotch Plains, N.J.

[73] Assignee: Colgate-Palmolive Company, New York, N.Y.

[21] Appl. No.: 307,271

[22] Filed: Sep. 30, 1981

[51] Int. Cl.³ .............................................. A61K 7/16
[52] U.S. Cl. ............................... 156/243; 156/244.11; 156/244.21; 156/244.25; 156/279; 156/500; 264/75; 264/101; 264/108; 424/49; 425/97; 425/130
[58] Field of Search ...................... 156/244.11, 244.25, 156/244.21, 276, 279, 280, 283, 500, 62.2, 243; 425/97, 105, 205, 215, 217, 222, DIG. 11, 130; 366/150, 151, 152, 153, 154, 155, 156, 157, 158, 159, 160, 177, 181; 424/49; 264/75, 101, 9, 108; 427/2, 420; 118/308, 310

[56] References Cited

U.S. PATENT DOCUMENTS

| | | | |
|---|---|---|---|
| 2,962,786 | 12/1960 | Hawk et al. | 156/244.25 |
| 3,219,507 | 11/1965 | Penman | 156/279 |
| 3,955,942 | 5/1976 | Cordon et al. | 424/49 |
| 4,003,971 | 1/1977 | Mannara | 264/9 |

Primary Examiner—Caleb Weston
Attorney, Agent, or Firm—Robert L. Stone; Herbert S. Sylvester; Murray M. Grill

[57] ABSTRACT

A method for manufacturing a dentifrice containing dispersed speckles or bits therein includes converting a gel or paste dental composition into flowing stream or ribbon form, directing a stream or curtain of speckle or bit particles onto the ribbon of dentifrice, to which such particles adhere, and controlling relative feed rates of the dentifrice and the speckles, so that there is produced a dentifrice containing the distributed speckles in desired proportion. Also described are apparatuses for carrying out the process.

11 Claims, 2 Drawing Figures

METHOD AND APPARATUS FOR MANUFACTURING DENTIFRICE CONTAINING DISPERSED SPECKLES

This invention relates to manufacturing dentifrices containing speckles or bits of dispersed materials. More particularly, it relates to making clear gel dentifrices containing evenly distributed and substantially evenly sized visible functional speckles which also give the dentifrice an attractive appearance.

Dentifrices in paste or gel form which contain dispersed speckles have been described in various patents, among which U.S. Pat. Nos. Re. 29,634; 3,711,604; 3,767,791; 3,803,301; 3,955,942; 4,003,971; and 4,089,943 may be taken as typical. Such products are also described in two U.S. patent applications filed the same day as this application by fellow Colgate-Palmolive Company researchers, Barth and Norfleet for one application and Hauschild and Principe for the other. Such patents and applications are incorporated herein by reference.

In the manufacture of speckled dentifrices it has been conventional to mix the speckles with the dental gel or paste, using conventional equipment, and to depend on the shearing actions of the mixers to distribute the speckles evenly throughout the dentifrice. While such technique may be a satisfactory one when the speckles are not frangible, when speckles that may be broken up or solubilized due to shearing actions of the mixer are to be blended with a dental composition results may be objectionable. Especially when such speckles include a finely divided functional material, such as a polishing agent, held in unitary aggregated but discrete form by a binder designed to be softened on storage, so that the speckles on use are distinct but impalpable, it is important to prevent mixing effects from causing the binder to soften or dissolve prematurely in the dentifrice or in a component thereof, and therefore product circulation, such as that resulting from the employment of conventional mixers, is to be avoided. In the past this problem has been solved by running mixers at low speed, thereby lengthening mixing times, but sometimes the permissible shearing forces were insufficient to break up clumps of speckles which may have been formed.

The present invention allows the manufacture of speckled dentifrices to be effected efficiently and quickly without the need for the use of any conventionally shearing mixing apparatus. Also, the speckles do not clump together and neither are they disintegrated, and because the process is a speedy one the product is quickly processed and may be filled into tubes before any appreciable softening or solubilizing of the dentifrice binder occurs. Thus, the preferred clear gel dentifrice, usually with individually visible, separate functional speckles attractively distributed therein, is obtained, without any clouding of it due to breaking up of speckles and distribution of the finely divided functional material, such as polishing agent, through the dentifrice.

Other advantages attendant the practicing of this invention include the immobilization of the speckles with respect to the gel ribbon, and resulting lesser dissolving of any binder utilized in any solvent materials that may be present in the gel. Also, the feeding of the gel in an arc that becomes vertical above a vessel outlet after the speckles have been deposited diminishes residence time in the apparatus before removal and thereby diminishes such dissolving of the binder for the speckles and prevents disintegration of the speckles.

In accordance with the present invention a method for manufacturing a dentifrice containing dispersed discrete speckles therein comprises producing a stream of a gel or paste dental composition containing a gelling agent which helps to make the surfaces thereof adhesive for the speckles, which dental composition constitutes a major proportion of the dentifrice, producing a stream of speckles to be distributed throughout the dentifrice, directing said stream of speckles onto a surface of the stream of the dental composition and controlling the relative feed rates and the proportions of the streams of dental composition and the speckles to be dispersed in the dentifrice so that when the stream of speckles contacts the stream of dental composition the speckles are insufficient to cover the dental composition surface, so that the speckles adhere to the dental composition stream and there is produced a dentifrice containing the speckles in desired proportion distributed in it. Also within the invention is an apparatus for carrying out the described process. Such apparatus comprises means for producing a moving or flowing stream of a dental composition, which is usually a dentifrice except for speckles to be distributed therein, and is of such a nature that the speckles will adhere to it. In such an apparatus a stream or ribbon of dental gel is produced by forcing it through an appropriate orifice so that it is extruded from said orifice in desired shape, preferably as a flat ribbon, the stream or curtain of speckles is of particle sizes within the No. 10 to 80 sieve range, U.S. Sieve Series, said speckles are directed onto the gel ribbon in such manner as to be distributed evenly over the inner portion of the surface of the flowing ribbon so as to adhere to said ribbon, and the ribbon of gel with adherent speckles thereon is collected in a walled vessel from which it is continuously removed as more gel containing speckles is added thereto or created therein.

Prior to the filling of this application a search was made in Subclasses 366-150, -151; -152; -153; -154; -155; -156; -157; -158; -159; -160; -177; and -181. No patents were found describing the present invention or making it obvious. The most relevant patents noted are U.S. Pat. Nos. Re. 27,681; 3,740,027; 3,948,491; 4,090,262; and 4,125,208. The reissue patent shows the dropping of a dry chemical from a hopper to a feeder, from which it is fed onto a stream or fan of liquid droplets, whereby each particle of the chemical is evenly wetted, and then enters a mixing solution in which it may be more quickly dissolved. U.S. Pat. No. 3,740,027 describes a particle wetting apparatus in which a dry powder is fed onto a revolving wetted roll from which the wetted particles are discharged into a body of the wetting liquid. U.S. Pat. No. 3,948,491 relates to blending a pigment into a plastic material by feeding it as a granular or powder material in separate charges into a bottom of a hopper through which the plastic material in granular or pellet form is fed. The pigment enters the hopper just before a stirrer, which is located just above the hopper discharge to a feed screw of a plastic molding machine. U.S. Pat. No. 4,090,262 discloses mixing and proportioning apparatus for making multicomponent plastic material mixes, with several metring mechanisms being positively coupled to each other so that the proportions of different components fed into a mixing chamber are kept constant. Finally, U.S. Pat. No. 4,125,208, which relates to supplying granular materials to processing machines, illustrates a charging hopper having a plurality of vacuum connections to it at different levels to withdraw objectionable gases from the material in the hopper so that a product made will be free of bubbles. None of these patents shows the structure of the apparatus of this invention and none shows the concept of the process, which is that dentifrice speckles may be individually and regularly deposited onto a moving flat ribbon of gelatinous paste dentifrice, to which such speckles will adhere, such depositing and the production of a speckled dentifrice being effected readily, and with the speckles being deposited in desired concentration and without clumping or disintegration of the speckles and without softening and solubilizing thereof during processing.

Figure 1:
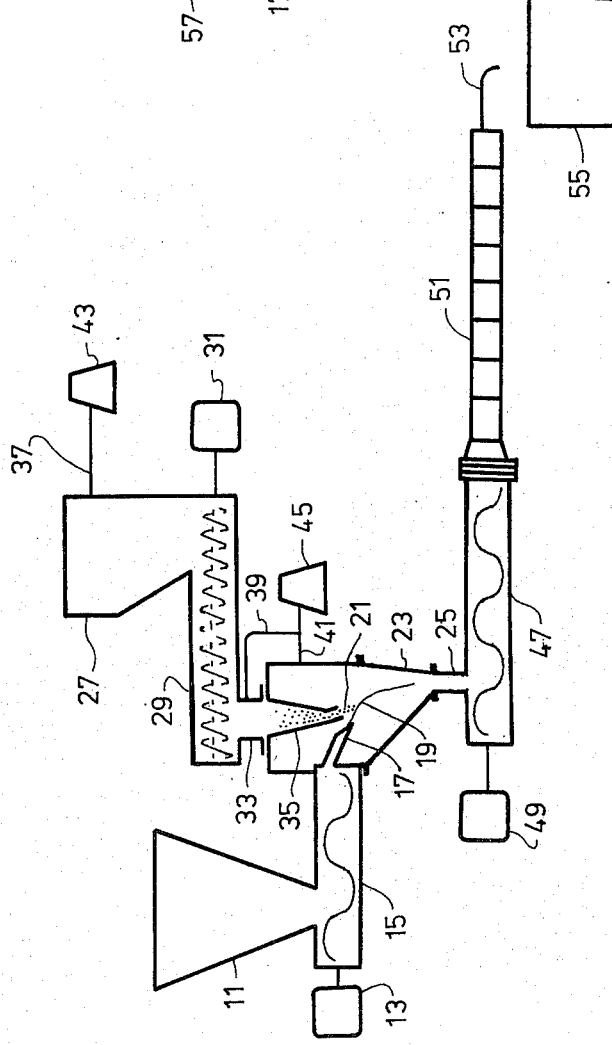

The invention will be readily understood from the present specification and the following detailed description of the drawing in which:

FIG. 1 is a schematic representation of an apparatus of this invention for making speckled dentifrice from a dental composition and previously produced speckles; and FIG. 2 is an enlarged perspective view of a portion of the "speckling apparatus" of this invention, illustrating application of speckles to a gel stream or ribbon.

In FIG. 1 there are shown gel-making vessel 11, which often preferably will be a Hobart or Dopp mixer, into which the various components of the dental composition, including vehicle, gelling agent, polishing agent, flavor, color, detergent, preservative and any other adjuvants, are mixed together, sometimes under vacuum, to form a composition to which speckles, preferably functional speckles, such as those based on a dental polishing agent, are to be added, to make a speckled dentifrice. Variable speed motor and/or drive 13 powers a positive displacement pump 15, at a controllable speed, to deliver the gel to an outlet 17, preferably a somewhat restricted flat orifice, through which it is extruded or discharged as a flat ribbon or other suitable stream 19 onto which speckles 21, in discrete bit or particulate form, are deposited. Pump 15 may be set to control the gel feed rate and by also controlling the feed rate of the speckles the desired proportion of speckles may be continuously added to the flowing gel. Preferably pump 15 will be one which subjects the gel to little or no shearing action, so as to maintain its consistency (viscosity), and screw pumps with walls of elastomer are preferred, such as those of the Moyno type. Gel feeding outlet means or extruder 17 is preferably enclosed in a walled vessel or container 23 and usually will be so positioned therein that ribbons of gel containing speckles on the surface thereof, produced in such vessel, will fall vertically to the bottom thereof near the center of the vessel, from which they may be removed through central outlet 25.

The speckles to be added to the dental gel in prescribed proportion are contained in a hopper 27 for a controllable flow rate feeder 29, preferably of a helix type, including speed control 31, which feeder discharges the speckles at a desired controlled rate through an outlet 33 onto a funnel shaped directing means 35, which shapes the discharge stream of speckles as desired so that as they leave it they form a falling stream or curtain which matches the ribbon of gel flowing from outlet 17, preferably being such that the speckles fall substantially vertically to deposit on and become adhered to the inner portion of the gel ribbon, with none missing contact with the gel. Preferably the speckle curtain covers a substantial part, e.g., 40 to 95%, preferably 60 to 90% of the width of the gel ribbon, and the curtain should not be so wide as to result in any substantial proportion of speckles missing the ribbon. However, it will be desirable to have the curtain be of a width only slightly less than the ribbon when feasible, e.g., 80 to 90%. Lines 37, 39 and 41 connect to vacuum sources 43 and 45, respectively but while the use of vacuum is desirable to prevent air bubbles from entering the dentifrice, with careful processing the infiltration of such bubbles may be avoided without the use of vacuum. After the speckled dentifrice is dropped through outlet 25, a pump 47, which is preferably a screw pump, such as one of the Moyno type, powered by variable speed motor 49, pumps the product in a gentle manner to static mixer 51, preferably of the Kenics type, where it is gently blended without disintegration or solubilization of the speckles therein, and is uniformly mixed. It then passes through line 53 to a receiver 55, which may be feed tank for a tube filling machine, not illustrated.

In FIG. 2 gel feeding means 57 includes a delivery tube 59 and a nozzle portion 17, with such nozzle including a flat rectangularly shaped opening 61. The gel feeding means and the opening in the discharge "nozzle" portion thereof may be adjustable. Thus, the feed direction could be changed as desired, and the angle of discharge could be varied but the feed direction should have a horizontal component and is usually from 0° to 45°, e.g., 10° to 30°, from the horizontal. Also, the rectangular orifice can be changed in size, so as to be more restricted, but care should be exercised to keep the gel ribbon coherent so the ribbon will not be thin beyond the gel strength. Usually it will be from 1 mm. to 1 cm. thick, e.g., 2 to 6 mm. The stream or ribbon of gel is directed so that the stream or curtain of speckles may fall on it correctly, preferably when the speckles are falling substantially vertically and the gel is moving in a direction with a horizontal component, so that the gel passes under the falling speckles, which contact it and adhere to it. The gel ribbon 63 is shown falling downwardly and to the right, while speckles 65 fall on to it from a discharge spout 67 of directing means 35 (FIG. 1).

In a preferred process of this invention a speckled clear gel dentifrice is made of the formula and by the method described in Example 1 of the U.S. patent application filed the same day as the present application by Barth and Norfleet. Because the formulations of the dental composition and the speckles are not parts of this invention they will not be detailed herein but it will be noted that the composition is adhesive with respect to the speckles, is preferably a coherent transparent gel and normally the proportion by weight of dentifrice speckles, such as those described in the referred to example, will be in the range 1 to 10%, preferably 2 to 5% of the finished dentifrice. Any of the usual gelling agents for aqueous dentifrices, such as sodium carboxymethyl cellulose (CMC), polyvinyl pyrrolidone, methyl cellulose, carrageenan, will normally make the aqueous dental composition sufficiently tacky in normal gelling concentrations, e.g., 0.2 to 1%. The various gel (or paste) components are mixed together in mixer 11 and are pumped, preferably by a Moyno type pump, to the extruder, which terminates in a flat "slit" nozzle, as illustrated, with a relatively narrow rectangular opening. Preferably, such a nozzle will be inclined downwardly from the horizontal at an angle of about 10° to 45°, e.g., 30°.

The feed rate of the speckle feeding mechanism, which is preferably an Acrisan helix feeder, is adjusted to correspond to the gel feed rate. Thus, when, for example, a 3% speckle content in the dentifrice is desired, if the feed rate of gel is 3 kilograms per minute, then the speckles will be fed at the rate of 93 grams per minute. Conventional electronic or mechanical means may be employed to maintain the desired feeds ratio, or to adjust it if changes in such proportions are desired for different products.

In the drawing the feeding mechanism for the speckles is shown only schematically in FIG. 1 and only the end thereof is shown in FIG. 2 but various types of feeds, including screw, belt, weighing belt, electronically controlled gravimetric feeders, and others may be used and the discharge pattern may be changed. The discharge will be such that few, if any, speckles will fall past the gel and the gel stream will hold the impinging speckles. Also, the speckles will fall separately and the gel will be moving fast enough underneath them, at a speed usually of 10 to 100 cm./second, e.g., 20 to 50 cm./sec., that individual speckles strike the gel and adhere to it, with very few hitting other held speckles and bouncing off them. Also, all or almost all of such bouncing speckles will subsequently adhere to the dental composition.

The falling speckled gel, with the speckles adherent to it, does not remain for a long period of time in the walled vessel in which or above which the speckling apparatus is located because it drops through the center of such vessel and most of it proceeeds almost directly to the outlet. (It is known that flow from a central outlet in a vessel containing a viscous or gelled material proceeds largely from the central core of any material contained in the vessel). This short residence time in the "speckling vessel" is highly desirable and helps to maintain the integrity of the speckles in the dentifrice. While residence times in the vessel may vary, typical times are in the range of 20 seconds to 2 minutes, the shorter the better. Such quick throughput, the absence of mobile speckles and the central gel discharge from the vessel also help to avoid aggregation of speckles into objectionable clumps. The additional volume of the walled vessel is for holding gel which may be fed into it during periods when filling equipment may be temporarily halted and before feed to the vessel can be stopped. Thus, often the walled vessel may contain only a small proportion of speckled gel, e.g., 10 to 25% of its volume. Alternatively, other material may act as a "wall" bounding the speckled gel, within the vessel.

After leaving the speckling vessel the gel is gently pumped by a Moyno type pump and passes through a static mixer, to assure complete mixing. The preferred static mixer, a Kenics mixer, is like that described in the Mar. 19, 1973 edition of Chemical Engineering in an article entitled *Handling Viscous Materials-Motionless Mixer for Viscous Polymers*. Although it is desirable to utilize a mixer prior to discharging the gel to a filling machine or suitable container before such machine, it is conceivable that the present process and apparatus, without such mixer, could sufficiently distribute the speckles throughout the gel, so that in some instances the mixer would not be employed.

The conditions of operations are not considered to be critical but it is usual that the vacuum employed will be within the range of about 300 to 700 mm. of mercury, e.g., 400 to 600 mm. Hg. Temperatures may be about room temperature or suitable elevated, as from 10° to 40° C. The pressure of extrusion of the gel varies with the gel viscosity but from 0.03 to to 0.7 kilograms per square centimeter appears to be a reasonable range.

The various pieces of equipment of this invention, because they are employed in processing an oral product, should be constructed of non-corroding and safe materials. It has been found that stainless steel components are highly preferable and the mixers, extruders, pumps and valves, and any other parts that contact liquid or gel materials, will preferably be made of stainless steel, such as is normally employed in the food processing industry.

When a 2% speckled clear dentifrice (containing silicon dioxide, sorbitol, glycerol, CMC, sodium lauryl sulfate, flavor and water in the gel, and alumina and ethyl cellulose in the speckles), like that described in Example 1 of the Barth-Norfleet patent application, previously referred to, is made by the method of this invention, utilizing the apparatus described herein, the product resulting will be just as desired, with the speckles being regularly distributed throughout the clear gel and with no cloudiness or disintegrated speckles noted. Similar results are obtainable when other speckled dentifrices described in the Barth-Norfleet patent application and the earlier mentioned patents are produced, utilizing the apparatus and process of this invention, as illustrated.

In practicing the inventive process, while it will be preferred for the dental gel or paste to be in flat ribbon form, it is understood that variations of such form may be utilized, such as arced ribbons and even cylindrical or tubular streams. Also, while it is preferred that the stream or curtain of speckles be a suitably thin straight curtain of such material, e.g., 0.1 mm. to 1 cm., e.g., 0.5 to 5 mm., in thickness, falling by gravity, the speckles may be forcefully directed onto the dentifrice. For example, in some instances, a vertically moving stream of dentifrice may have speckles directed onto it horizontaly, with those not adhering being collected for recycling. The dental material stream may be given a rotary motion so that it "picks up" about its entire exposed surface speckles unidirectionally aimed at it. Conveyed speckle particles could impact a gel stream and deposit on it, immobile and discrete. Yet, while such variations of the invention are operative, the method described and illustrated herein is considered to be much superior.

The proportion of speckles fed to the moving ribbon or web of gel dentifrice will be a minor proportion, compared to the complete dentifrice containing speckles, and compared to the gel fed. (All percentages and proportions mentioned in the specification are by weight, unless otherwise indicated). The feed rate for the speckles will usually be adjusted so that the amount of speckles directed onto the gel will be insufficient to cover it and preferably will be insufficient to cover more than half the area of the portion of the gel exposed to the curtain of speckles when such curtain contacts the gel. While, as was mentioned previously, different ways of adhering the speckles to the gel ribbon have been mentioned, it is highly preferable that the speckles be dropped vertically in a curtain onto a ribbon of gel, with the gel moving in a direction with a horizontal component. Such direction may be horizontal or have a significant horizontal component with the gel falling after having picked up the speckles, but normally an inclination from the horizontal will be preferred for the gel, with the speckles falling vertically, after having been discharged from a delivery apparatus. The viscosity of the gel is not critical, so long as the speckles sufficiently adhere to it, and the sizes of the particles are not critical, but normally they are in the No's. 10 to 80 sieve size range, preferably 30 to 80, and more preferably 30 to 60. The speckles are preferably sharp edged and in falling onto the gel stream they become partially embedded therein, immediately being rendered immobile, but similar good results may also be obtained when rounded speckles are used. Although the speckles used are preferably visible in a clear gel, which makes the product aesthetically attractive, they may be of an index of refraction which renders them invisible. Thus, the designation "speckles" includes visible and invisible discrete particles of various materials, with agglomerates of finely divided polishing agents being preferred. Also, while it is preferred that they be agglomerates of finely divided polishing agent and binder they may comprise other "active" components, such as therapeutic agents, colorants, flavors and fluorides.

It is contemplated that the dentifrice material on which speckles are deposited will be all the dentifrice, except speckles, but this is not necessary. It is possible that some dental components may be blended in with the other dentifrice materials after addition of the speckles. For example, it may be desirable to blend in the flavoring, which may contain some volatile components, before the Kenics mixer but after any application of vacuum to the product during the depositing of the speckles. Such a procedure would have the advantages of preserving the flavor, preventing losses of more volatile components thereof due to the application of the vacuum in the speckling operation, and any flavor components which would solubilize the binder of the speckles would have less processing time contact with them. Yet, the Kenics or other relatively low shear static mixer would blend the flavoring evenly throughout the dentifrice. Similarly, other components, usually minor adjuvant components, could be added to the dentifrice subsequent to the incorporation of the speckles therein.

The walled vessel mentioned, into which the speckled dentifrice falls, may be under vacuum or may be opened to the atmosphere. The speckling apparatus may have a reservoir underneath it, rather than being enclosed in a vessel. However, it is preferred that such equipment be covered, under vacuum, when air entrapment would otherwise be a problem, and act as a container for the speckling apparatus, in addition to being a vessel to hold the product made. The present process and apparatus lend themselves to use for making a variety of different dentifrice formulas containing different proportions of speckles. To vary the speckles concentration is a simple matter, since it involves only changing the speed of the speckles feeder and controlling the gel feed rate accordingly.

Among the various advantages of the invention are increased efficiency of operation, diminution of employment of moving part mixers and the stabilization of the dental gel or paste. It is known that various dentifrices are thinned by excessive mechanical working and the present blending operation for adding speckles to the dentifrice avoids such working and allows maintenance of the desired viscosity of the dental gel.

The present invention has been described with respect to various examples and preferred embodiments thereof but is not to be limited to these because it is evident that one of skill in the art, with the present specification before him, would be able to utilize substitutes and equivalents without departing from the invention.

What is claimed is:

1. A method for manufacturing a dentifrice containing dispersed discrete speckles therein which comprises producing a stream of a gel or paste dental composition continuously flowing in a direction having downward and horizontal components, which dental composition constitutes a major proportion of the dentifrice and contains a gelling agent which helps to make surfaces thereof adhesive for the speckles, producing a stream of speckles to be distributed throughout the dentifrice, directing said stream of speckles downwardly onto a surface of the stream of the dental composition and controlling the relative feed rates and the proportions of the streams of dental composition and the speckles to be dispersed in the dentifrice so that when the stream of speckles contacts the stream of dental composition the speckles are insufficient to cover the dental composition surface, so that the speckles adhere to the dental composition stream and there is produced a dentifrice containing the speckles in desired proportion distributed in it.

2. A method according to claim 1 wherein the stream of gel or paste dental composition is a ribbon of gel, continuously flowing downwardly in a direction having a horizontal component, the stream of speckles is in the form of a falling curtain directed so as to fall downwardly onto the flowing gel ribbon and the amount of speckles in the falling curtain is insufficient to cover more than half of the area of the ribbon surface presented to it.

3. A method according to claim 2 wherein the gel or paste dental composition constitutes all the dentifrice except for the speckles to be distributed therein, the ribbon of such gel is produced by forcing it through a suitably shaped orifice so that it is extruded from said orifice as a ribbon, the curtain of speckles is of particle sizes within the No. 10 to 80 sieve range, U.S. Sieve Series, said speckles are directed onto the gel ribbon in such manner as to be distributed evenly over a substantial portion of the width of the flowing ribbon and adhered to said ribbon, and the ribbon of gel with adherent speckles thereon is collected in a walled vessel from which it is continuously removed as additional gel containing speckles is added thereto.

4. A method for manufacturing a dentifrice containing dispersed discrete speckles therein which comprises producing a ribbon of gel for the dentifrice, which gel constitutes all the dentifrice except for the speckles, and which contains a gelling agent which helps to make surfaces thereof adhesive for the speckles, by forcing the gel through a suitably shaped orifice so that it is extruded from said orifice as a ribbon in a direction having a horizontal component, which ribbon falls into a walled vessel at an angle with a horizontal component, producing a falling curtain of speckles to be distributed throughout the dentifrice, directing said falling curtain of speckles, of particle sizes within the No's. 10 to 80 sieve range, U.S. Sieve Series onto a surface of the flowing gel ribbon in such manner as to be distributed evenly over a substantial proportion of the width of the flowing ribbon and be adhered to said ribbon, with the curtain of speckles contacting the ribbon of gel as such ribbon falls into a walled vessel at an angle with a horizontal component, after which contact the ribbon falls vertically into the walled vessel, and controlling the relative feed rates and the proportions of the ribbon of gel and the curtain of speckles to be dispersed in the dentifrice so that when the curtain of speckles contacts the ribbon of gel the speckles are insufficient to cover more than half of the area of the ribbon surface presented to the curtain of speckles, so that the ribbon of gel with adherent speckles thereon is collected in the walled vessel, from which it is continuously removed as additional gel containing speckles is added thereto.

5. A method according to claim 4 wherein the streams of gel and speckles and the walled vessel are under vacuum during the making of the speckles dentifrice, and the speckled gel resulting is withdrawn from the walled vessel by means of an elastomer-lined screw pump, mixed in a static mixer and fed to a container for subsequent transfer to a tube filling machine.

6. An apparatus for manufacturing a dentifrice containing dispersed speckles therein which comprises means for producing a downwardly flowing freely falling stream of gel or paste dental composition, means for producing a freely falling stream of speckles to be distributed throughout a dentifrice and for directing said stream onto a surface of the stream of dental composition, where such speckles will be held without compressing, and means for controlling relative feed rates and proportions of the dental composition and the speckles to be dispersed therein, so that when the stream of speckles contacts the stream of dental composition the speckles are insufficient to cover the dental composition surface, the speckles adhere to the dental composition stream and there is produced a dentifrice containing speckles in desired proportion distributed in it.

7. An apparatus according to claim 6 wherein the means for producing a stream of dental composition is capable of producing a ribbon of gel continuously downwardly flowing in a direction having a horizontal component, the means for producing a stream of speckles and directing them onto the surface of the ribbon of gel produces a curtain of the speckles and directs them so that they fall downwardly onto the flowing gel ribbon and the means for controlling the relative feed rates and proportions of the gel and speckles controls them so that the amount of speckles in the falling curtain is insufficient to cover more than half of the surface of the gel ribbon.

8. An apparatus for manufacturing a dentifrice containing dispersed speckles therein which comprises an extruder for producing a continuously downwardly flowing gel or paste dental composition ribbon which is flowing in a direction having a horizontal component, a helix or screw feeder and distributing means for producing a curtain of speckles to be distributed through the dentifrice and for directing said curtain so that the speckles fall downwardly onto the flowing gel ribbon where they will be held, means for controlling relative feed rates and proportions of the dental composition and the speckles to be dispersed therein so that when the curtain of speckles contacts the stream of dental composition the speckles are insufficient to cover more than half of the surface of the composition ribbon, and a walled vessel above which or in which the means for extruding the dental composition ribbon and the means for producing the curtain of speckles are located.

9. An apparatus according to claim 8 wherein the means for producing the curtain of speckles directs such speckles downwardly so that they fall in a vertical curtain onto the gel ribbon, the walled vessel has an outlet opening at the bottom thereof, and the means for producing the gel ribbon directs it so that after the speckles contact the ribbon and are held by it, it falls vertically toward the outlet from the walled vessel.

10. An apparatus according to claim 9 comprising means for maintaining the walled vessel under vacuum.

11. An apparatus according to claim 10 including a screw pump and a static mixer, the screw pump being located in communication with an outlet from the walled vessel in which the speckled dentifrice is made so as continuously to withdraw the dentifrice from such vessel and pump it through the static mixer without disintegrating or dissolving speckles thereof in the dentifrice, so that the dentifrice may be delivered to a tube filling machine without objectionable change in the appearance in the speckles.

* * * * *